(12) United States Patent
Pao et al.

(10) Patent No.: US 9,314,176 B2
(45) Date of Patent: Apr. 19, 2016

(54) APPARATUS AND METHOD FOR PROCESSING SIGNAL

(75) Inventors: Sun-Hua Pao, Taipei (TW); Chieh-Neng Young, Tainan (TW); Tsung-Min Hsieh, Tainan (TW); Yio-Wha Shau, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 1036 days.

(21) Appl. No.: 13/450,930

(22) Filed: Apr. 19, 2012

(65) Prior Publication Data

US 2012/0310600 A1  Dec. 6, 2012

Related U.S. Application Data

(60) Provisional application No. 61/491,410, filed on May 31, 2011.

(30) Foreign Application Priority Data

Dec. 20, 2011 (TW) .............................. 100147515 A

(51) Int. Cl.
*H03F 1/26* (2006.01)
*A61B 5/04* (2006.01)
*H03H 17/02* (2006.01)
(Continued)

(52) U.S. Cl.
CPC ......... *A61B 5/04004* (2013.01); *A61B 5/04017* (2013.01); *A61B 5/725* (2013.01); *H03H 17/0261* (2013.01); *A61B 5/04325* (2013.01); *A61B 2560/0475* (2013.01)

(58) Field of Classification Search
None
See application file for complete search history.

(56) References Cited

U.S. PATENT DOCUMENTS

| 4,455,862 A * | 6/1984 | Takeuchi | F02P 5/152 73/35.03 |
|---|---|---|---|
| 5,983,162 A | 11/1999 | Huang | |
| 6,311,130 B1 | 10/2001 | Huang | |

(Continued)

FOREIGN PATENT DOCUMENTS

| CN | 101872425 A | 10/2010 |
|---|---|---|
| TW | 200410115 A | 6/2004 |

(Continued)

OTHER PUBLICATIONS

Full English (machine) translation of CN1032288 (Published Apr. 12, 1989).

(Continued)

*Primary Examiner* — Aditya Bhat
(74) *Attorney, Agent, or Firm* — McClure, Qualey & Rodack, LLP

(57) ABSTRACT

An apparatus and a method for processing signal are provided. The signal processing apparatus comprises an input interface and a processing unit. The input interface receives smoothing parameters and a to-be-separated signal. The processing unit establishes an upper extreme envelope and a lower extreme envelope of the to-be-separated signal, and calculates a mean envelope between the upper extreme envelope and the lower extreme envelope. The processing unit performs smoothing according to the smoothing parameters and the mean envelope to generate a smoothed mean envelope, and determines a trend component or a non-trend component according to the smoothed mean envelope.

27 Claims, 14 Drawing Sheets

(51) Int. Cl.
*A61B 5/00* (2006.01)
*A61B 5/0432* (2006.01)

(56) References Cited

U.S. PATENT DOCUMENTS

| | | | |
|---|---|---|---|
| 6,381,559 B1 | 4/2002 | Huang | |
| 6,631,325 B1 | 10/2003 | Huang et al. | |
| 6,738,734 B1 | 5/2004 | Huang | |
| 6,901,353 B1 | 5/2005 | Huang | |
| 7,060,035 B2 * | 6/2006 | Wasserman | A61B 5/04017 600/300 |
| 7,647,209 B2 | 1/2010 | Sawada et al. | |
| 2002/0191314 A1 * | 12/2002 | Ottesen | G11B 5/012 360/31 |
| 2003/0033094 A1 | 2/2003 | Huang | |
| 2003/0058964 A1 | 3/2003 | Ezquerra-Moreu et al. | |
| 2010/0179974 A1 | 7/2010 | Pao et al. | |
| 2010/0217093 A1 | 8/2010 | Ko et al. | |
| 2011/0158259 A1 | 6/2011 | Chen et al. | |
| 2011/0261977 A1 | 10/2011 | Hiroe | |

FOREIGN PATENT DOCUMENTS

| | | |
|---|---|---|
| TW | 200707405 | 2/2007 |
| TW | 200746044 | 12/2007 |
| TW | 201016190 A | 5/2010 |
| TW | 201027361 A1 | 7/2010 |
| TW | 201028126 A1 | 8/2010 |

OTHER PUBLICATIONS

English Abstract translation of CN101872425 (Published Oct. 27, 2010).
English Abstract translation of TW201028126 (Published Aug. 1, 2010).
English Abstract translation of TWI274269 (TW200410115, published Jun. 16, 2004).
English language translation of abstract of TW 200707405 (published Feb. 16, 2007).
English language translation of abstract of TW 200746044 (published Dec. 16, 2007).
Huang, N.E., et al.; "The Empirical Mode Decomposition and the Hilbert Spectrum for Nonlinear and Non-Stationary Time Series Analysis;" Proceedings of the Royal Society; 2012; pp. 902-995.
Blanco-Velasco, M., et al.; "ECG Signal Denoising and Baseline Wander Correction Based on the Empirical Mode Decomposition;" Computers in Biology and Medicine 38; 2008; pp. 1-13.
Sun, J., et al.; "A Hybrid Detrending Method for Fractional Gaussian Noise;" Physica A; 2011; pp. 2995-3001.
Bahsan, A., et al.; "Comparison of Detrending Methods for Fluctuation Analysis;" Physica A; 2008; pp. 5080-5090.
Moghtaderi, A., et al.; "Trend Filtering via Empirical Mode Decompositions;" Computational Statistics and Data Analysis; pp. 1-13.
Wu, Z., et al.; "On the Trend, Detrending, and Variability of Nonlinear and Nonstationary Time Series;" Applied Mathematics; 2007; pp. 14889-14894.
Montesino, F., et al.; "Effect of Different Detrending Approaches on Computational Intelligence Models of Time Series;" IEEE; 2010; pp. 1-8.
Yeh, J.R., et al.; "Human Heart Beat Analysis Using a Modified Algorithm of Detrend Fluctuation Analysis Based on Empirical Mode Decomposition;" Medical Engineering & Physics 31; 2009; pp. 92-100.
Shafqat, F.K., et al.; "Evaluation of Two Detrending Techniques for Application in Heart Rate Variability;" Proceedings of the 29th Annual International Conference of the IEEE EMBS; 2007; pp. 267-270.
Qin, Y., et al.; "A New Method for Multicomponent Signal Decomposition Based on Self-Adaptive Filtering;" Measurement 44; 2011; pp. 1312-1327.
Cheng, J., et al.; "Application of Frequency Family Separation Method Based Upon EMD and Local Hilbert Energy Spectrum Method to Gear Fault Diagnosis;" Mechanism and Machine Theory 43; 2008; pp. 712-723.

* cited by examiner

APPARATUS AND METHOD FOR PROCESSING SIGNAL

This application claims the benefit of U.S. provisional application Ser. No. 61/491,410, filed May 31, 2011, and the benefit of Taiwan application Serial No. 100147515, filed Dec. 20, 2012, the subject matters of which are incorporated herein by reference.

BACKGROUND

1. Technical Field

The disclosed embodiments relate in general to a signal processing method and a signal processing apparatus.

2. Description of the Related Art

Referring to FIGS. 10-16. FIG. 10 shows a 10 Hz sine wave. FIG. 11 shows a sine wave of 2 Hz. FIG. 12 shows a trend line. FIG. 13 shows a mixture of 10 Hz and 2 Hz waves. FIG. 14 shows a corresponding spectrum of FIG. 13. FIG. 15 shows a trend signal and a mixture of 10 Hz and 2 Hz waves with the trend signal. FIG. 16 shows a corresponding spectrum of FIG. 15. The horizontal coordinate of FIGS. 10-15 denotes the time index of a signal, and the vertical coordinate of FIGS. 10-15 denotes the magnitude of the signal. The horizontal coordinate of FIGS. 14 and 16 denotes the frequency (Hz) of the signal, and the vertical coordinate of FIGS. 14 and 16 denotes the amplitude of the signal spectrum. The physiological signal is normally captured through an electrode, and further intensified and amplified to an acceptable range by a front-end amplifier. Then, the signal of the interference source is filtered by a filter to obtain a signal of interest. Lastly, the analog signal is converted into a digital signal for subsequent processing by an analog-to-digital converter. The specification of the capturing parameter, the design of the filter and the design of the rear-end hardware such as recorder, alarm system and wireless transmission are dependent on the application.

Natural signals normally contain the information of various time scales, which may cover different frequency bands, have different energy distributions and specific wave patterns. These signals are basically divided into the periodic component and the aperiodic component, wherein the aperiodic component, such as denoting the trend, discontinuity, and stochasticity. When such signals are analyzed by fast Fourier transform (FFT), the spectrum may be contaminated by the aperiodic trend line. As illustrated in FIGS. 13-16, the trend line not only affects the low-frequency part of the spectrum, but also affects the entire spectrum. Such spectrum problems cannot be resolved by conventional filtering method. The influence on the spectrum by the trend can only be relieved by analyzing the time signal.

The trend indicates the overall tendency of the signal, while the other periodic components are the fluctuation overriding the trend signal. The magnitude of the fluctuation of the signal cannot be easily obtained without prior understanding of the trend. On the other hand, if the trend signal is not processed properly, the spectrum will be contaminated and subsequent signal processing will be troublesome.

When developing the application of physiological signal technology, the capturing of the physiological signal must be resolved first before the characteristics of the signal can be analyzed. However, the same physiological signal applied in different applications requires different signal processing methods to perform better. In the analysis of electrocardiography signal, for example, the properties of signal distribute wildly from high to low frequency. For the application of heart rate measurement, one can filter out all components except the QRS complex. Although the filtered signal is distorted significantly, the heart rate still can be effectively monitored as long as R waves are recognizable. When it comes to monitoring the variation in particular wave patterns such as ST-elevations and the variation in the QT intervals, careful filtering is required to assure the recognizability of these specific wave patterns. For example, low-frequency baseline wandering may easily affect the wave pattern of low-frequency T wave, and make the wave pattern unrecognizable.

On the other hand, when the conventional FFT method is used for calculating the spectrum, the input signal is assumed to repeat periodically and the periodic length is equal to the length of the signal. However, if the true signal is not periodic or the assumed periodic length is incorrect, this requirement may cause leakage issue due to boundary condition. Origin supports the use of window functions to mitigate the leakage. Several functions are supported, including Triangular, Bartlett, Hann, Hamming and so on. Although these window functions can deal with the boundary condition, the interference of low-frequency diffusion still occurs to the spectrum, and the effect of adding a window affects energy estimation in main frequencies. Thus, the influence of trend signal cannot be easily resolved in the frequency domain directly or indirectly. A thorough solution lies in obtaining the real trend signal from the original signal.

SUMMARY

The disclosure is directed to a signal processing method and a signal processing apparatus.

According to one embodiment, a signal processing method. The signal processing method comprises the following steps of: receiving smoothing parameters and a to-be-separated signal; establishing an upper extreme envelope and a lower extreme envelope of the to-be-separated signal; calculating a mean envelope between the upper extreme envelope and the lower extreme envelope; smoothing the mean envelope according to the smoothing parameters and the mean envelope to generate a smoothed mean envelope; and determining a trend component or a non-trend component according to the smoothed mean envelope.

According to another embodiment, a signal processing apparatus. The signal processing apparatus comprises an input interface and a processing unit. The input interface receives the smoothing parameters and a to-be-separated signal. The processing unit establishes an upper extreme envelope and a lower extreme envelope of the to-be-separated signal, and calculates a mean envelope between the upper extreme envelope and the lower extreme envelope. The processing unit performs smoothing according to the smoothing parameters and the mean envelope to generate a smoothed mean envelope, and determines a trend component or a non-trend component according to the smoothed mean envelope.

According to an alternative embodiment, a signal processing apparatus is provided. The signal processing apparatus comprises a signal sensing unit and an output interface. The signal sensing unit generates a to-be-separated signal according to a physiological signal. The output interface outputs the to-be-separated signal to the functional chip to determine a trend component or a non-trend component.

Figure 1:
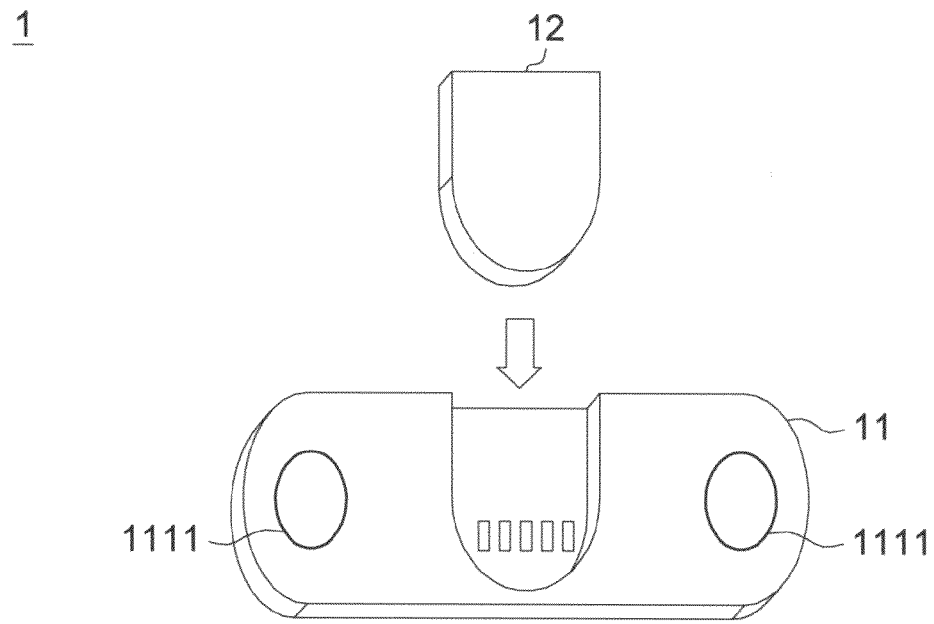
FIG. 1 shows an exterior diagram of a signal processing apparatus in accordance with an embodiment.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Figure 2:
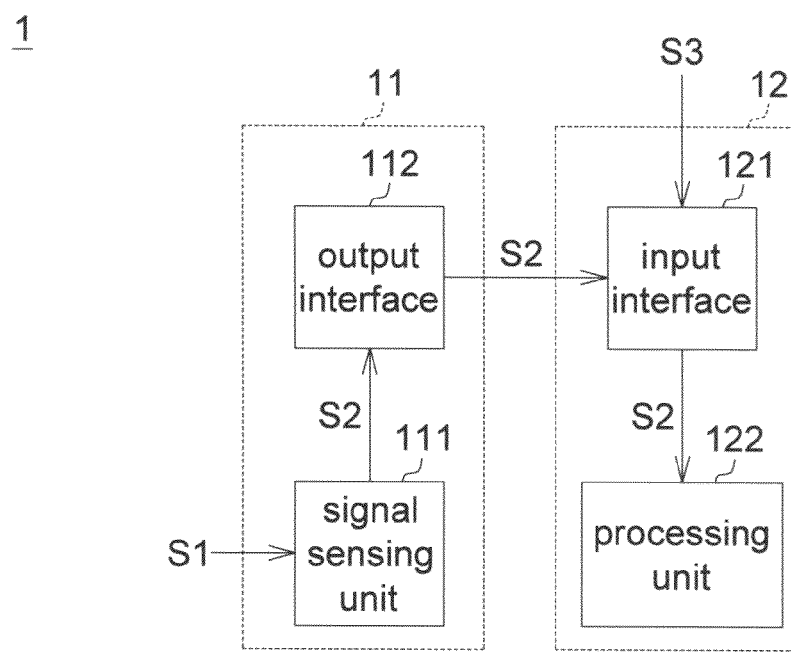
FIG. 2 shows a block diagram of a signal processing apparatus in accordance with an embodiment.
Figure 3:
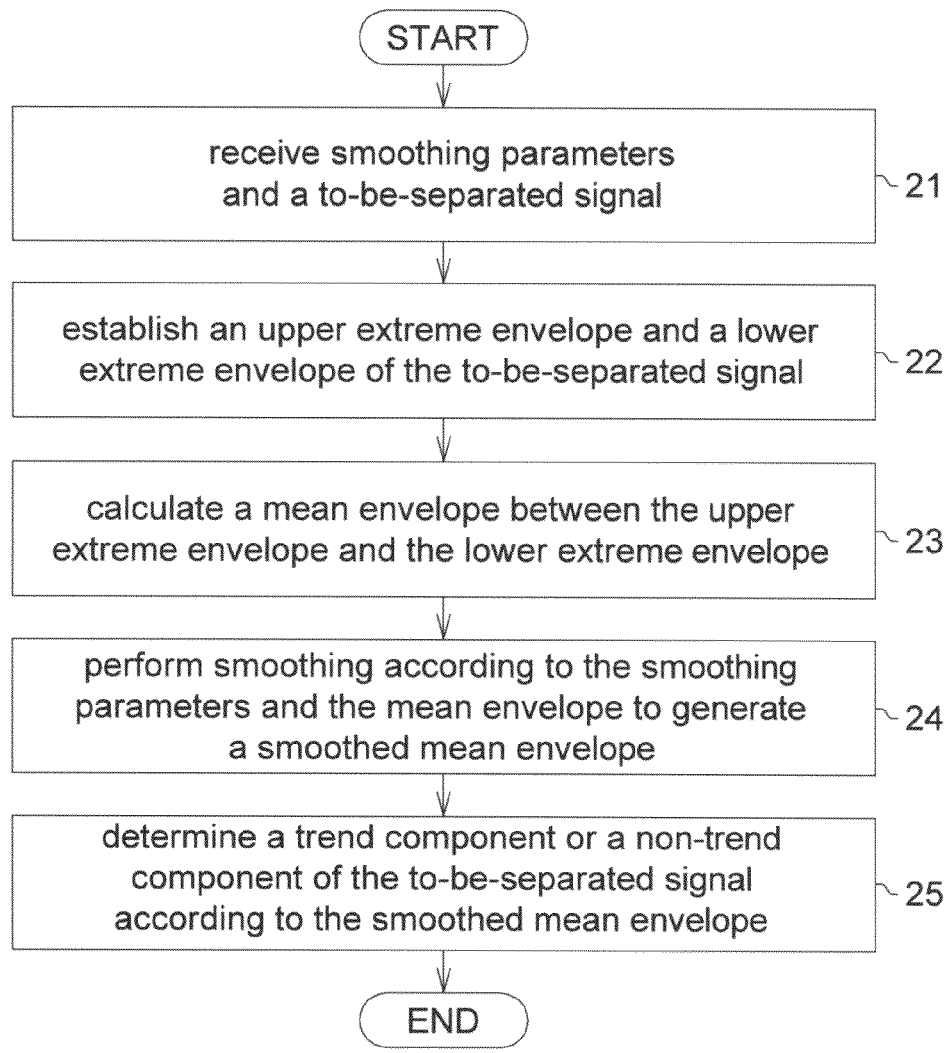
FIG. 3 shows a flowchart of a signal processing method.
Figure 4:
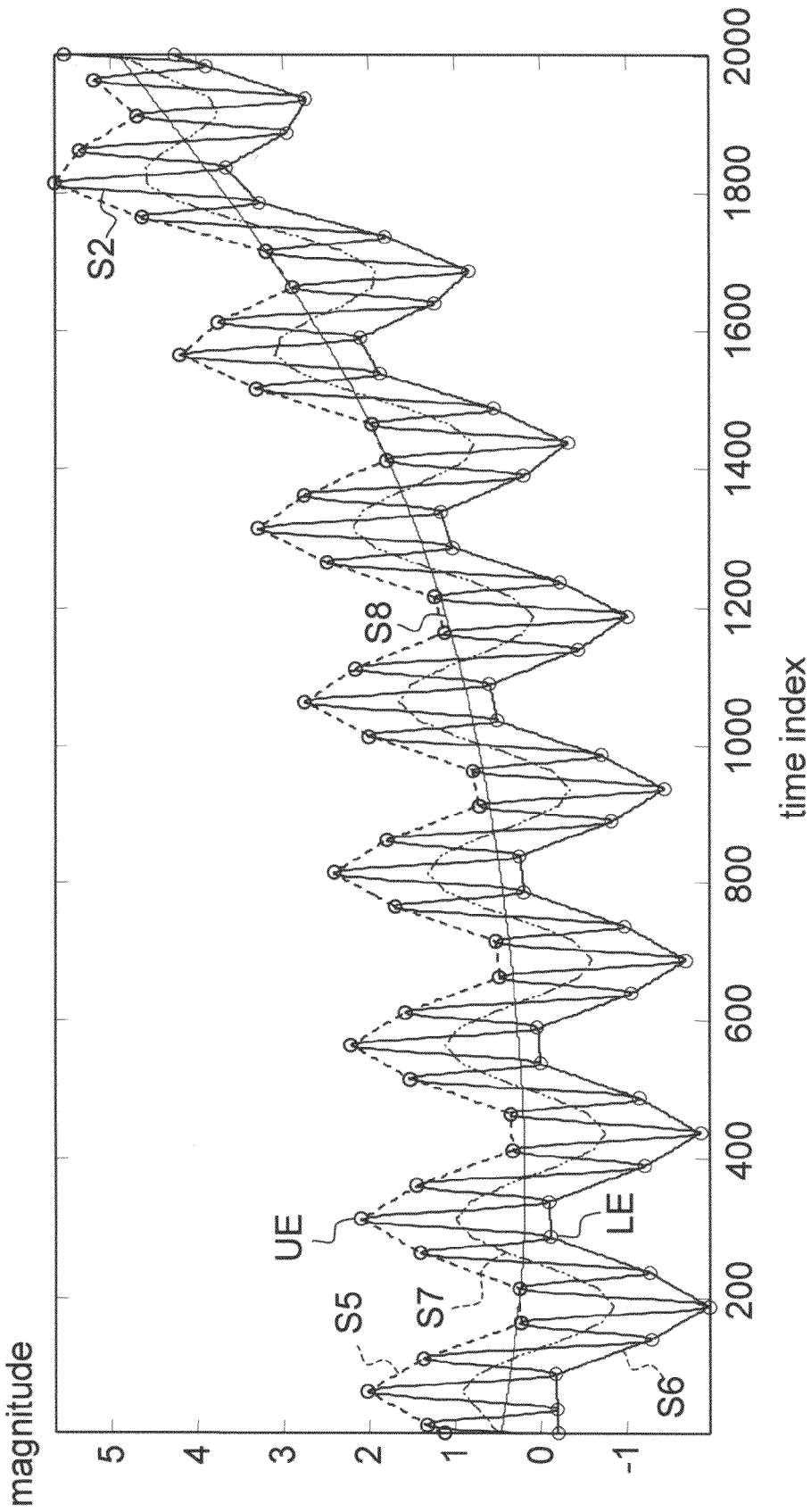
FIG. 4 shows a to-be-separated signal, an upper extreme envelope, a lower extreme envelope, a mean envelope and a smoothed mean envelope.
Figure 5:
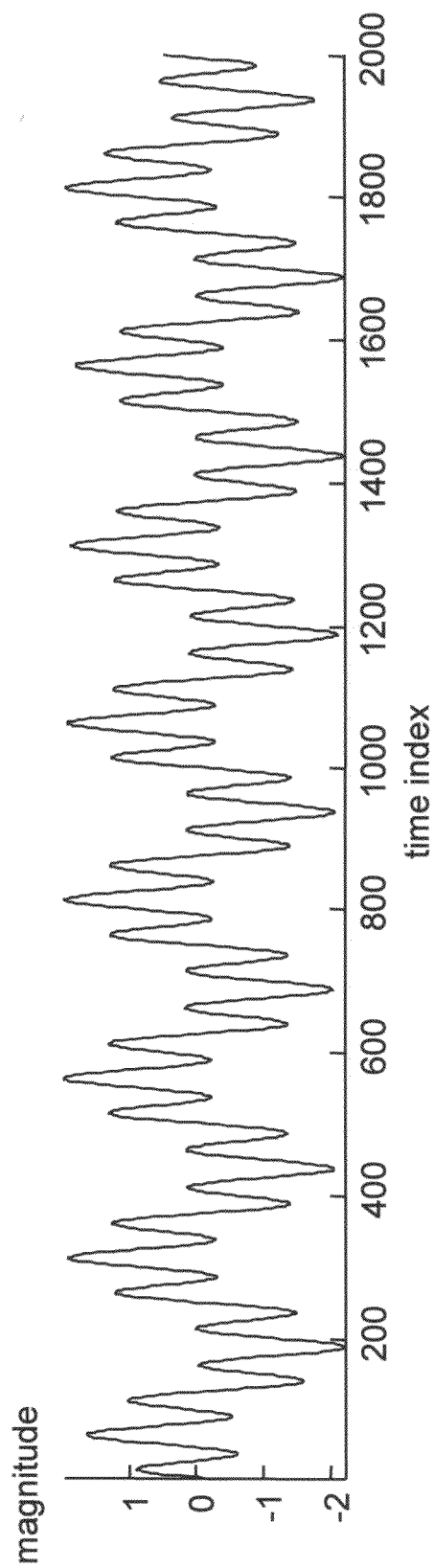
FIG. 5 shows a non-trend component.

Referring to FIG. 1, FIG. 2, FIG. 3, FIG. 4 and FIG. 5. FIG. 1 shows an exterior diagram of a signal processing apparatus in accordance with an embodiment. FIG. 2 shows a block diagram of a signal processing apparatus in accordance with an embodiment. FIG. 3 shows a flowchart of a signal processing method. FIG. 4 shows a to-be-separated signal, an upper extreme envelope, a lower extreme envelope, a mean envelope and a smoothed mean envelope. FIG. 5 shows a non-trend component. The horizontal coordinate of FIG. 5 denotes the time index of the signal, and the vertical coordinate of FIG. 5 denotes the magnitude of the signal. The signal processing apparatus 1 comprises a chip carrier 11 and a functional chip 12 according to the design of a pluggable physiological signal carrier. Examples of the physiological signal S1 include electrocardiography, electromyography, electroencephalography, electrooculography, body temperature information signal, motion signal or audio signal. After the functional chip 12 is inserted into the chip carrier 11, the physiological signal can be measured accordingly. User can choose corresponding functional chip 12 for other types of to-be-measured physiological signals S1. Thus, the chip carrier 11 can be repeatedly used for saving resources. When the signal processing apparatus 1 is used in the field of medical care, different types of functional chips 12 can be provided with respect to different symptoms. The doctor can provide a corresponding functional chip 12 according to the patient's situation. When the patient is at home, the patient can insert the functional chip 12 to the chip carrier 11 to achieve at-home monitoring.

In an embodiment, the chip carrier 11 comprises a signal sensing unit 111 and an output interface 112. In other words, the signal sensing unit 111 and the output interface 112 are integrated as a chip carrier 11. The signal sensing unit 111 generates a to-be-separated signal S2 according to the physiological signal S1, and the output interface 112 outputs the to-be-separated signal to the functional chip 12 to determine the trend component or the non-trend component of the to-be-separated signal S2. The functional chip 12 comprises an input interface 121 and a processing unit 122. In other words, the input interface 121 and the processing unit 122 are integrated as a functional chip. FIG. 2 shows only the input interface 121 and the processing unit 122. In other embodiments, elements with other functions such as storage, alarm, compression, transmission, the heart rate monitoring or abnormality detection can also be added to the functional chip 12.

In an embodiment, the signal processing method is applicable to the signal processing apparatus 1, and comprises the following steps. In step 21, the input interface 121 receives smoothing parameters S3 and a to-be-separated signal S2. The smoothing parameters S3 can be flexibly adjusted by the user according to the characteristics of the to-be-measured physiological signal. The smoothing parameters S3 comprises such as the frequency range, the smooth window width, the smoothing iterations and the boundary processing method, and the user can determine the frequency range. The boundary processing method is such as reflection symmetry or 2-fold rotational symmetry. Let a one-dimensional time series be taken for example. Reflection symmetry refers to the extension of boundary along the time axis by performing one-to-one mirror-image copy from the end of the signal. 2-fold rotational symmetry refers to the extension of boundary along the time axis by performing one-to-one anti-mirror-image copy from the end of the signal. That is, the duplicated signal is the same with part of original signal after being rotated 180 degrees around the end point.

In step 22, the processing unit 122 establishes an upper extreme envelope S5 and a lower extreme envelope S6 of the to-be-separated signal S2. In step 23, the processing unit 122 calculates a mean envelope S7 between the upper extreme envelope S5 and the lower extreme envelope S6. In step 24, the processing unit 122 performs smoothing according to the smoothing parameters S3 and the mean envelope S7 to generate a smoothed mean envelope S8.

The adjustment of the smoothing parameters is based on the to-be-separated signal S2. Let the to-be-separated signal S2 be f(t) and the smooth window width be 2n+1, then the smoothing computation formula is expressed as:

$$\text{SMOOTH}(f(t)) = \sum_{i=0}^{2n} w_i \cdot f(t+i-n), \text{ where } \sum_{i=0}^{2n} w_i = 1.0.$$

According to Fourier analysis, the function f(t) is expressed as:

$$f(t) = \sum_{i=0}^{\infty} (a_i \cos\omega_i t + b_i \sin\omega_i t).$$

After smoothing once, the signal of the smooth window 2n+1 can be expressed as:

$$\bar{f}(t) = \frac{1}{n} \sum_{i=0}^{\infty} \sum_{k=-\frac{n-1}{2}}^{\frac{n-1}{2}} (a_i \cos\omega_i(t+kT) + b_i \sin\omega_i(t+kT)),$$

wherein T denotes the time interval between time index, and can also be expressed as:

$$\bar{f}(t) = \sum_{i=0}^{\infty} \left( \frac{1}{n} \cdot \left( 1 + 2 \sum_{k=1}^{(n-1)/2} \cos\omega_i kT \right) \right) \cdot f(t).$$

After R times of smoothing, the signal can be expressed as:

$$\bar{f}(t) = \sum_{i=0}^{\infty} \left( \frac{1}{n} \cdot \left( 1 + 2 \sum_{k=1}^{(n-1)/2} \cos\omega_i kT \right) \right)^R \cdot f(t)$$

or $$\bar{f}(t) = \sum_{i=0}^{\infty} F(\omega_i, n, R) \cdot (a_i \cos\omega_i t + b_i \sin\omega_i t).$$

As indicated above, the signal smoothed once and the to-be-separated signal S2 have the same constituting spectrum except that the signal smoothed once shows amplitude decays in the high-frequency components. In the present embodiment of the invention, the intensity of decay is used as a reference for determining whether the level of smoothness is suitable, and the user can select and extract the needed trend component with reference to the spectrum distribution of the to-be-separated signal S2. The decay formula is expressed as:

$$F(\omega_i, n, R) = \left( \frac{1}{n} \cdot \left( 1 + 2 \sum_{k=1}^{(n-1)/2} \cos\omega_i kT \right) \right)^R, 0 \le \omega_i T \le \pi,$$

wherein $\omega_i$ denotes a frequency range; n denotes a smooth window width; R denotes a smoothing iterations.

In step 25, the processing unit 122 determines the trend component or the non-trend component of the to-be-separated signal S2 according to the smoothed mean envelope S8. The trend component is obtained by accumulating all smoothed mean envelopes or performing weight computation according to the difference between the smoothed mean envelope S8 and the to-be-separated signal S2. In step 25, the processing unit 122 determines whether the smoothed mean envelope S8 converges. If the smoothed mean envelope S8 does not converge, then the processing unit 122 repeats steps 22 to 24 after removing the smoothed mean envelope S8 from the to-be-separated signal S2. To the contrary, if the smoothed mean envelope S8 already converges, the processing unit 122 again determines the trend component or the non-trend component of the to-be-separated signal S2 according to the smoothed mean envelope S8. The trend component can be regarded as an indicator of the aggregate tendency of the to-be-separated signal S2, and the non-trend component is the fluctuation overriding the trend component. Once the change in the trend component is obtained, the processing unit 122 will be able to identify the magnitude of the signal fluctuating on the trend component. For example, the processing unit 122 can remove the trend component according to the smoothed mean envelope S8 to obtain the non-trend component of FIG. 5.

The processing unit 122 can determine whether the smoothed mean envelope S8 converges by different ways. For example, the processing unit 122 determines whether the smoothed mean envelope converges according to Cauchy convergence test. Or, the processing unit 122 can determines whether the standard deviation of the smoothed mean envelope S8 is smaller than a default threshold or not. If the standard deviation of the smoothed mean envelope S8 is smaller than default threshold, the processing unit 122 determines that the smoothed mean envelope S8 has already converged. To the contrary, if the standard deviation of the smoothed mean envelope S is not smaller than the default threshold, the processing unit 122 determines that the smoothed mean envelope S8 does not converge.

Figure 6:
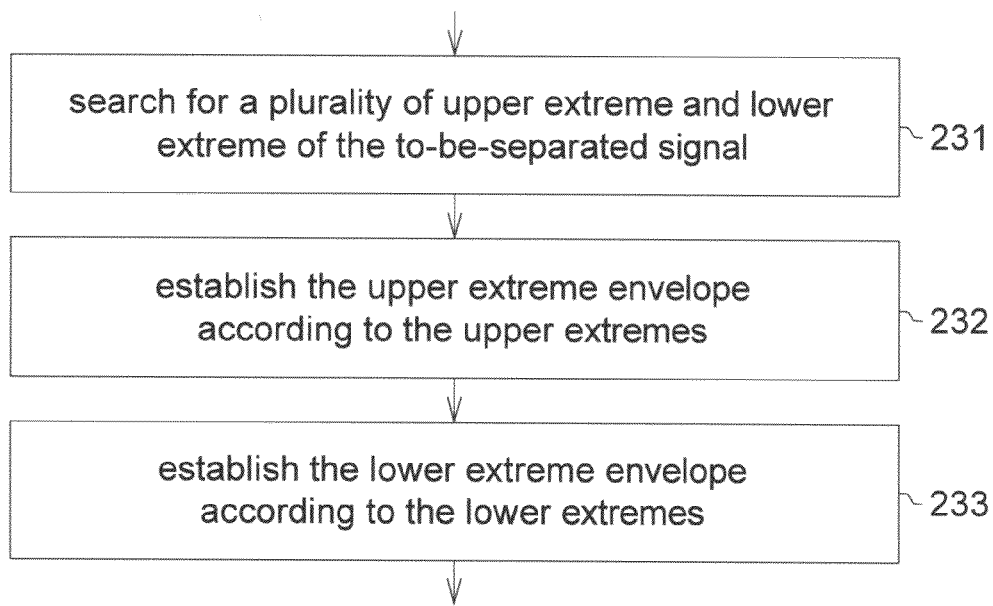
FIG. 6 shows a detailed flowchart of step 23.

Referring to FIG. 2, FIG. 3, FIG. 4 and FIG. 6. FIG. 6 shows a detailed flowchart of step 23. The horizontal coordinate of FIG. 4 denotes the time index of the signal, and the vertical coordinate of FIG. 4 denotes the magnitude of the signal. The above-mentioned step 23 further comprises steps 231 to 233. In step 231, the processing unit 122 searches for upper extremes UE and lower extremes LE of the to-be-separated signal S2. The upper extremes UE and the lower extremes LE are the local maxima and the local minima of the to-be-separated signal S2 respectively. In step 232, the processing unit 122 establishes the upper extreme envelope S5 according to the upper extremes UE. In step 233, the processing unit 122 establishes the lower extreme envelope S6 according to the lower extremes LE.

Figure 7:
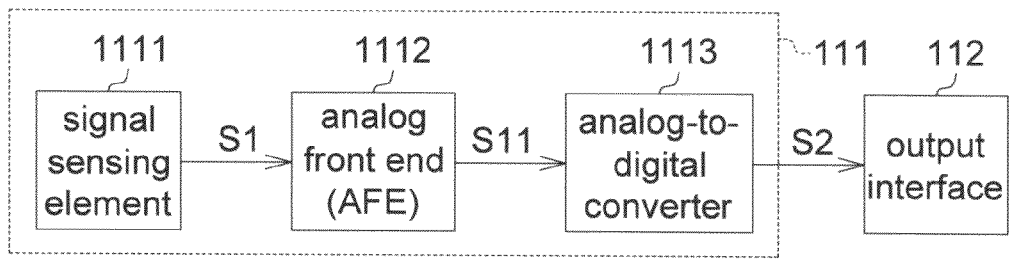
FIG. 7 shows a passive sensing element in accordance with an embodiment.

Referring to FIG. 7, a passive sensing element in accordance with an embodiment is shown. The signal sensing unit 111 comprises a signal sensing element 1111, an analog front end (AFE) 1112 and an analog-to-digital converter 1113. The signal sensing element 1111 is, for example, either a passive sensing element or an active sensing element. The passive sensing element is such as an electrode, a thermistor, a thermocouple, an accelerometer or a microphone. The signal sensing unit 111 can measure a physiological signal such as electro-cardiogram, electro-myogram, electroencephalogram, and electro-oculogram with electrodes, and measure information such as temperature and respiratory flow with a thermistor or thermocouple. Besides, the signal sensing unit 111 can further measure a motion signal with an accelerometer and measures an audio signal with a microphone.

The signal sensing element 1111 measures a physiological signal S1. The analog front end 1112 is coupled to the signal sensing element 1111 for amplifying the physiological signal S1 to generate an analog signal S11. The analog-to-digital converter 1113 converts the analog signal S11 into a digitalized to-be-separated signal S2. The output interface 112 is coupled to the analog-to-digital converter 1113 for outputting the to-be-separated signal S2 to an input interface 121 of the functional chip 12. The transmission of signal between the output interface 112 and the input interface 121 can be either contact type or non-contact type. If the transmission of signal between the output interface 112 and the input interface 121 is contact type, then the output interface 112 and the input interface 121 can be realized by electrical contacts. If the transmission of signal between the output interface 112 and the input interface 121 is non-contact type, then the output interface 112 and the input interface 121 can be realized by Bluetooth modules or wireless transmission modules.

Figure 8:
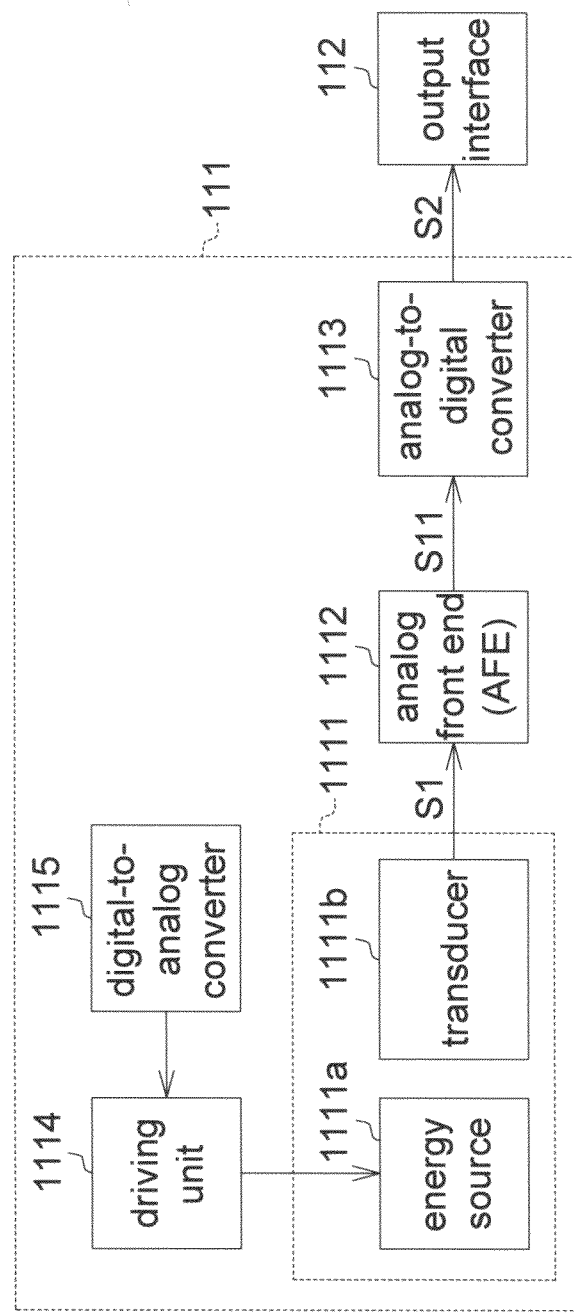
FIG. 8 shows an active sensing element in accordance with an embodiment.

Referring to FIG. 8, an active sensing element in accordance with an embodiment is shown. If the signal sensing element 1111 is an active sensing element, then the signal sensing unit 111 further comprises a driving unit 1114 and a digital-to-analog converter 1115. The driving unit 1114 is used for driving the signal sensing element 1111. For example, the signal sensing element 1111 comprises an energy source 1111a and a transducer 1111b. The functional chip 12 generates a control command for controlling the driving unit 1114 via the digital-to-analog converter 1115. The driving unit 1114 applies the energy source 1111a to the human body, and the transducer 1111b generates the physiological signal S1.

The signal sensing unit 111 generates the to-be-separated signal S2 through the analog front end 1112 and the analog-to-digital converter 1113 to complete the signal capturing function. The energy source 1111a and the transducer 1111b are paired up in use. For example, when blood oxygen saturation is measured by photoplethysmography, the energy source 1111a can be realized by light emitting diodes (LEDs) capable of emitting the lights of different wavelengths, and the transducer 1111b can be realized by photodiodes capable of detecting the luminance.

Figure 9:
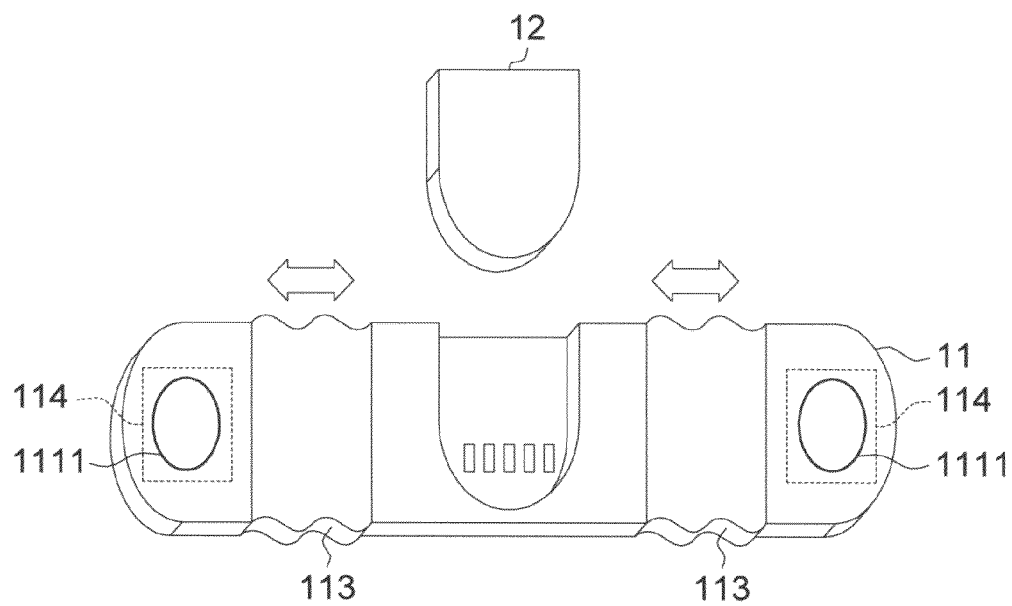
FIG. 9 shows an exterior diagram of another signal processing apparatus in accordance with an embodiment.
Figure 10:
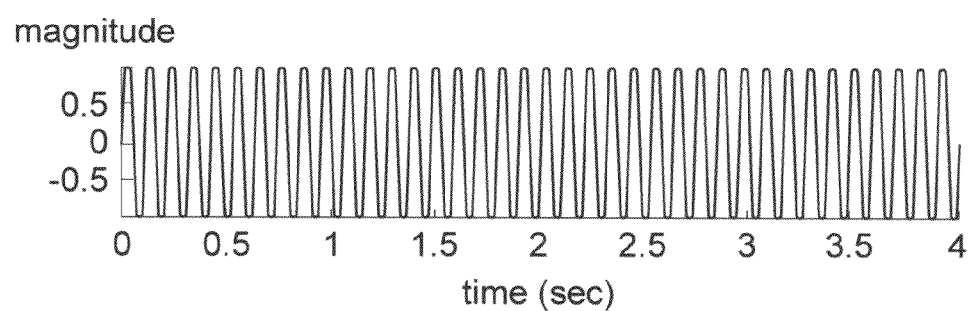
FIG. 10 shows a 10 Hz sine wave.
Figure 11:
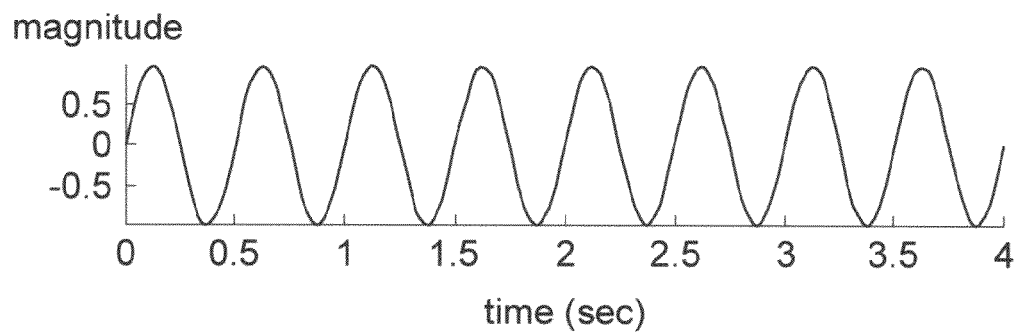
FIG. 11 shows a sine wave at 2 Hz.
Figure 12:
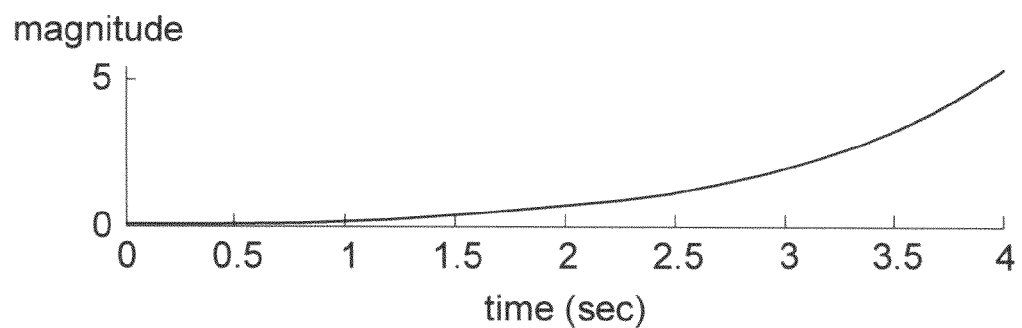
FIG. 12 shows a trend signal.
Figure 13:
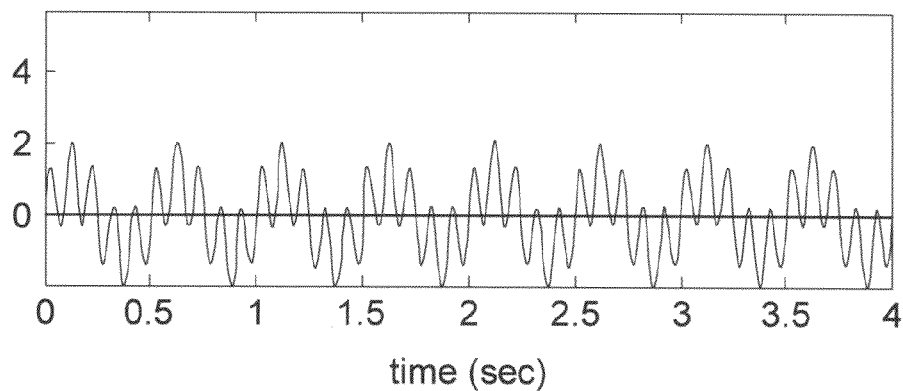
FIG. 13 shows a mixture of 10 Hz and 2 Hz waves.
Figure 14:
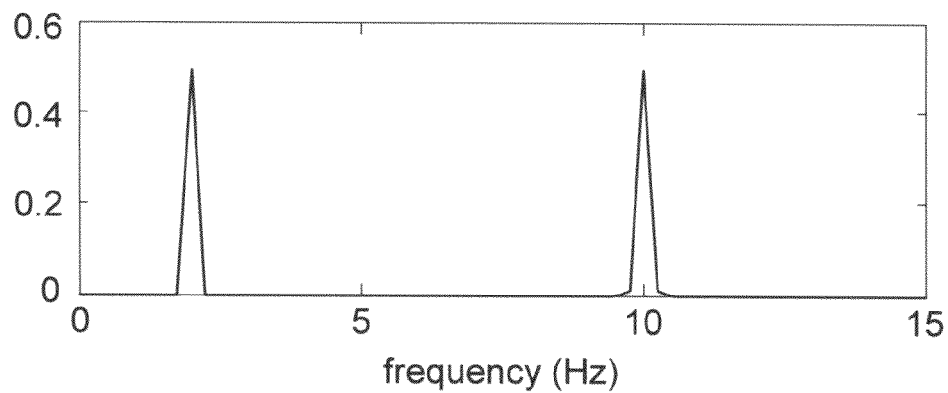
FIG. 14 shows the corresponding spectrum of FIG. 13.
Figure 15:
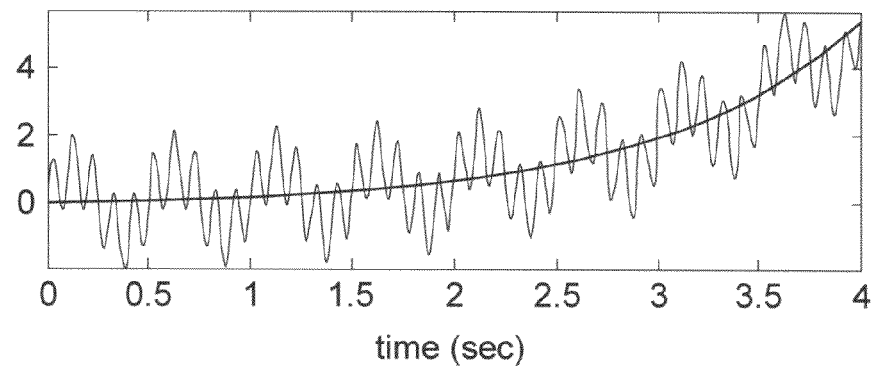
FIG. 15 shows a trend signal and a mixture of 10 Hz and 2 Hz waves with the trend signal.
Figure 16:
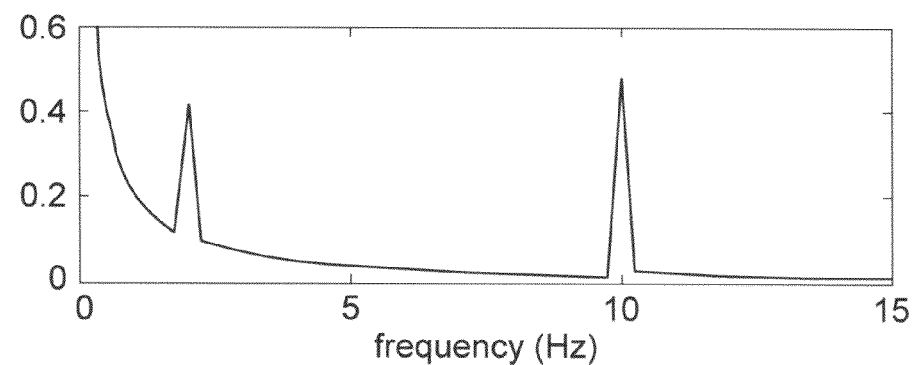
FIG. 16 shows the corresponding spectrum of FIG. 15.

Referring to FIG. 9, an exterior diagram of another signal processing apparatus in accordance with an embodiment is shown. The chip carrier of the signal processing apparatus further comprises a stretchable portion 113 and an adhesive positioning portion 114. The stretchable portion 113 is used for extending the signal sensing element 1111, and the adhesive positioning portion 114 is set around the signal sensing element 1111. The user may extend the signal sensing element 1111 outward to a suitable position by extending the stretchable portion 113. Furthermore, the user may use the adhesive positioning portion 114 for fixing the signal sensing element 1111 at a suitable position.

Figure 17:
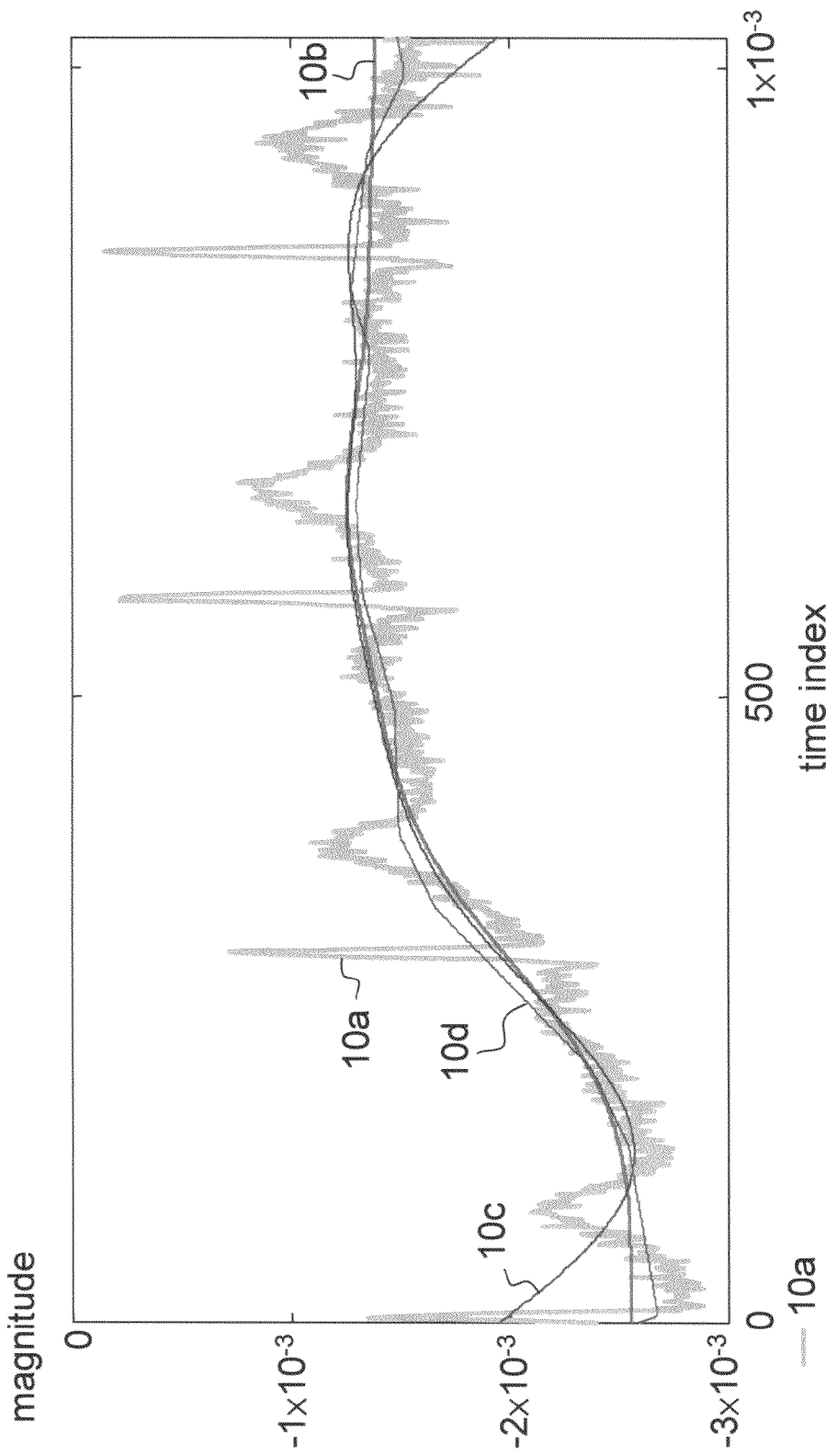
FIG. 17 shows a trend component of an electrocardiography signal.
Figure 18:
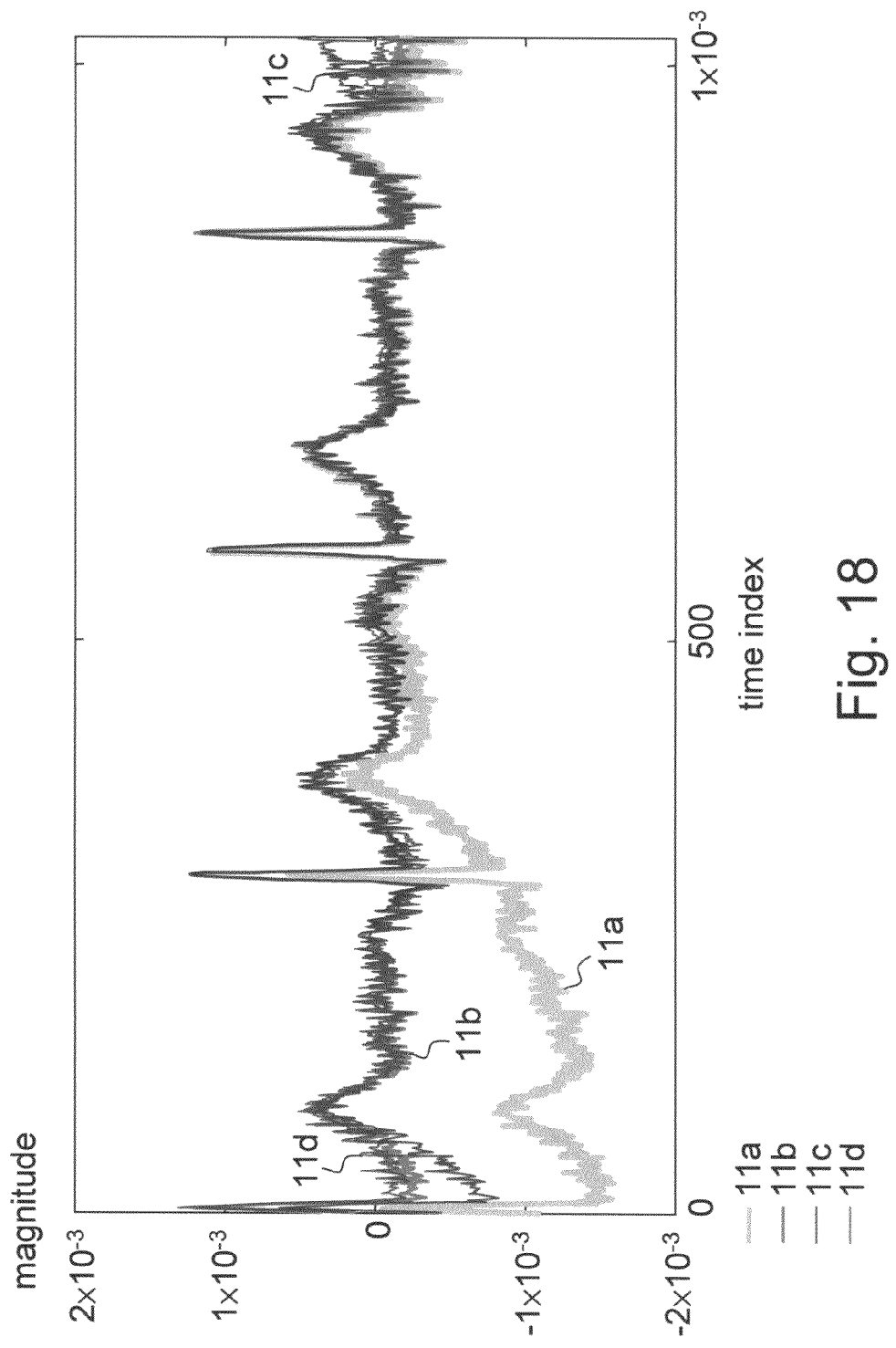
FIG. 18 shows a non-trend component of an electrocardiography signal.

Referring to FIG. 17 and FIG. 18. FIG. 17 shows a trend component of an electrocardiography signal. FIG. 18 shows a non-trend component of an electrocardiography signal. The horizontal coordinate of FIG. 17 and FIG. 18 denotes the time index of the signal, and the vertical coordinate of FIG. 17 and FIG. 18 denotes the magnitude of the signal. The electrocardiography signal 10a, filtered by the signal processing apparatus of the above-mentioned embodiments, generates a trend component 10b. The electrocardiography signal 10a, filtered by a conventional IGF filter, generates a trend component 10c. The electrocardiography signal 10a, filtered by a conventional EMD filter, generates a trend component 10d. It is noted that the trend component 10c and the trend component 10d generated by the conventional IGF filter and the conventional EMD filter respectively are distorted and may be easily affected by boundary conditions. Relatively, the trend component 10b generated by the signal processing apparatus of the above-mentioned embodiments is less likely to be affected by boundary conditions and signal distortion can thus be avoided.

The electrocardiography signal 11a, filtered by the signal processing apparatus of the above-mentioned embodiments, generates a non-trend component 11b. The electrocardiography signal 11a, filtered by a conventional IGF filter, generates a non-trend component 11c. The electrocardiography signal 11a, filtered by a conventional EMD filter, generates a non-trend component 11d. It is noted that the non-trend component 11c and non-trend component 11d generated by the conventional IGF filter and the conventional EMD filter respectively are distorted and may be easily affected by boundary conditions. Relatively, the non-trend component 11b generated by the signal processing apparatus of the above-mentioned embodiments is less likely to be affected by boundary conditions and signal distortion can thus be avoided.

Figure 19:
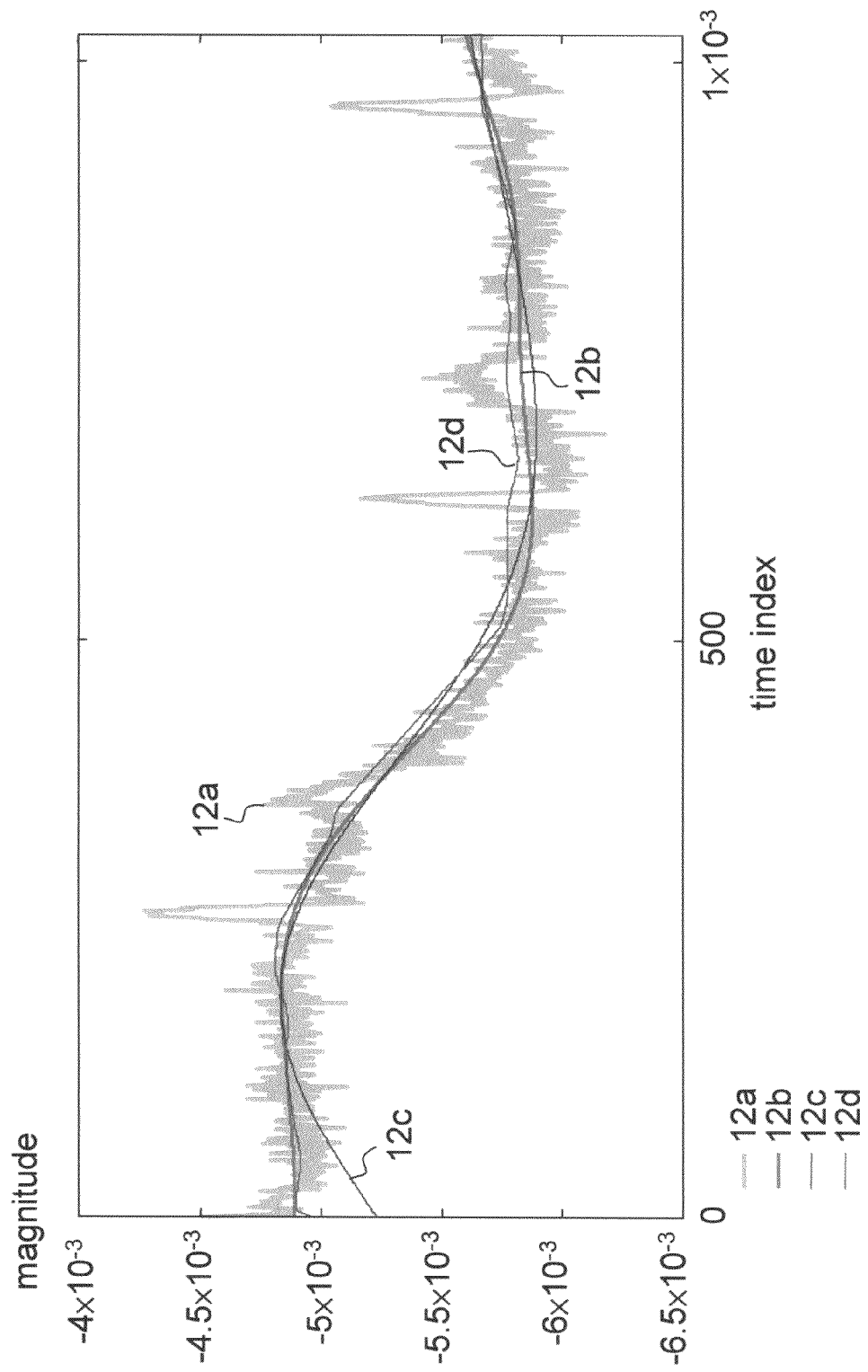
FIG. 19 shows a trend component of another electrocardiography signal.
Figure 20:
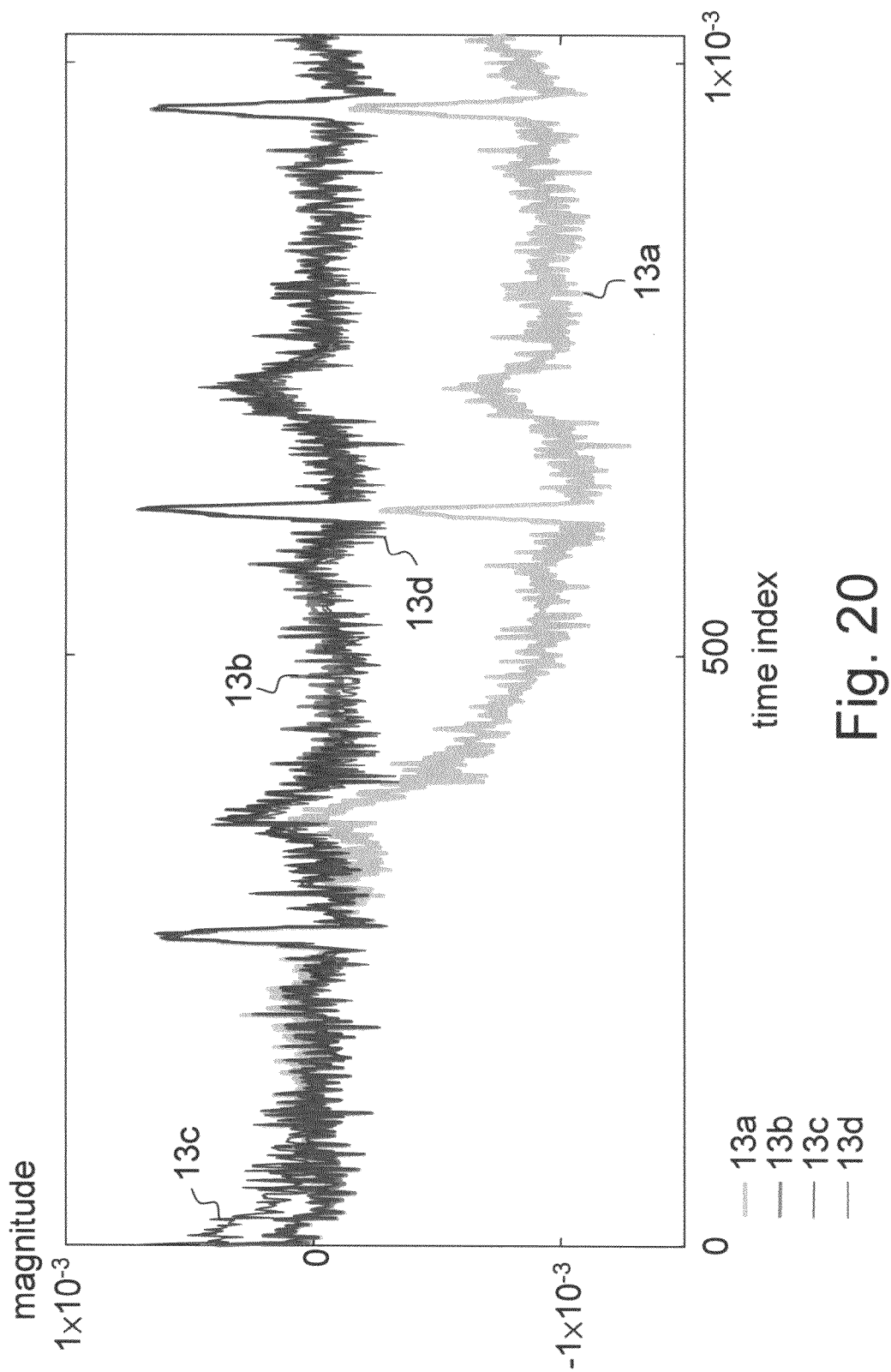
FIG. 20 shows a non-trend component of another electrocardiography signal.

Referring to FIG. 19 and FIG. 20. FIG. 19 shows a trend component of another electrocardiography signal. FIG. 20 shows a non-trend component of another electrocardiography signal. The horizontal coordinate of FIG. 19 and FIG. 20 denotes the time index of the signal, and the horizontal coordinate of FIG. 19 and FIG. 20 denotes the magnitude of the signal. The electrocardiography signal 12a, filtered by the signal processing apparatus of the above-mentioned embodiments, generates a trend component 12b. The electrocardiography signal 12a, filtered by a conventional IGF filter, generates a trend component 12c. The electrocardiography signal 12a, filtered by a conventional EMD filter, generates a trend component 12d. It is noted that the trend component 12c and the trend component 12d respectively generated by the conventional IGF filter and the conventional EMD filter are distorted and may be easily affected by a nonperiodic baseline drift. Relatively, the trend component 12b generated by the signal processing apparatus of the above-mentioned embodiment is less likely to be affected by aperiodic baseline drift and signal distortion can thus be avoided.

The electrocardiography signal 13a, filtered by the signal processing apparatus of the above-mentioned embodiments, generates a non-trend component 13b. The electrocardiography signal 13a, filtered by a conventional IGF filter, generates a non-trend component 13c. The electrocardiography signal 13a, filtered by a conventional EMD filter, generates a non-trend component 13d. It is noted that the non-trend component 13c and the non-trend component 13d generated by the conventional IGF filter and the conventional EMD filter respectively are distorted and may be easily affected by a nonperiodic baseline drift. Relatively, the non-trend component 13b generated by the signal processing apparatus of the above-mentioned embodiments is less likely to be affected by aperiodic baseline drift and signal distortion can thus be avoided.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A signal processing method, comprising:
  receiving smoothing parameters and a to-be-separated signal, wherein the to-be-separated signal is generated according to a physiological signal, and the smoothing parameters are adjusted according to the physiological signal;
  establishing an upper extreme envelope and a lower extreme envelope of the to-be-separated signal, wherein the upper extreme envelope and the lower extreme envelope respectively represent every local maxima and every local minima of the to-be-separated signal;
  calculating a mean envelope between the upper extreme envelope and the lower extreme envelope;
  performing smoothing according to the smoothing parameters and the mean envelope to generate a smoothed mean envelope;
  determining a trend component or a non-trend component of the to-be-separated signal according to the smoothed mean envelope, wherein the trend component represents tendency of the to-be-separated signal, and the non-trend component of the to-be-separated signal represents fluctuation on the trend component; and using the trend component to represent a physiological signal of a patient representative of a health aspect of the patient.

2. The signal processing method according to claim 1, wherein the establishing step comprises:
   searching for a plurality of upper extremes and lower extremes of the to-be-separated signal;
   establishing the upper extreme envelope according to the upper extremes; and
   establishing the lower extreme envelope according to the lower extremes.

3. The signal processing method according to claim 1, wherein the smoothing parameters comprise a smooth window width, a smoothing iteration and a boundary processing method.

4. The signal processing method according to claim 3, wherein the boundary processing method is reflection symmetry or 2-fold rotational symmetry.

5. The signal processing method according to claim 1, wherein the determination step comprises:
   determining whether the smoothed mean envelope converges;
   repeating the establishing step, the calculation step and the smoothing step after removing the smoothed mean envelope from the to-be-separated signal if the smoothed mean envelope does not converge; and
   determining the trend component or the non-trend component of the to-be-separated signal according to the smoothed mean envelope if the smoothed mean envelope converges.

6. The signal processing method according to claim 5, wherein the determination step comprises:
   determining whether the standard deviation of the smoothed mean envelope is smaller than a default threshold;
   determining that the smoothed mean envelope converges if the standard deviation of the smoothed mean envelope is smaller than the default threshold; and
   determining that the smoothed mean envelope does not converge if the standard deviation of the smoothed mean envelope is not smaller than the default threshold.

7. The signal processing method according to claim 5, wherein in the determination step, whether the smoothed mean envelope converges is determined according to Cauchy convergence test.

8. The signal processing method according to claim 1, wherein the trend component accumulates smoothed mean envelopes.

9. The signal processing method according to claim 1, wherein the trend component is obtained from a weight computation according to the difference between smoothed mean envelopes and the to-be-separated signal.

10. A signal processing apparatus, comprising:
    an input interface used for receiving smoothing parameters and a to-be-separated signal, wherein the to-be-separated signal is generated according to a physiological signal, and the smoothing parameters are adjusted according to the physiological signal; and
    a processing unit used for
    establishing an upper extreme envelope and a lower extreme envelope of the to-be-separated signal, wherein the upper extreme envelope and the lower extreme envelope respectively represent every local maxima and every local minima of the to-be-separated signal,
    calculating a mean envelope between the upper extreme envelope and the lower extreme envelope, wherein the processing unit performs smoothing according to the smoothing parameters and the mean envelope to generate a smoothed mean envelope, and determines a trend component or a non-trend component of the to-be-separated signal according to the smoothed mean envelope, wherein the trend component represents tendency of the to-be-separated signal, and the non-trend component of the to-be-separated signal represents fluctuation on the trend component; and
    using the trend component to represent a physiological signal of a patient representative of a health aspect of the patient.

11. The signal processing apparatus according to claim 10, wherein the processing unit searches for a plurality of upper extremes and lower extremes of the to-be-separated signal, establishes the upper extreme envelope according to the upper extremes, and establishes the lower extreme envelope according to the lower extremes.

12. The signal processing apparatus according to claim 10, wherein the smoothing parameters comprise a smooth window width, a smoothing iteration and a boundary processing method.

13. The signal processing apparatus according to claim 12, wherein the boundary processing method is reflection symmetry or 2-fold rotational symmetry.

14. The signal processing apparatus according to claim 10, wherein the processing unit determines whether the smoothed mean envelope converges, if the smoothed mean envelope does not converge, then the processing unit re-establishes the upper extreme envelope and the lower extreme envelope and re-calculates the mean envelope after removing the smoothed mean envelope from the to-be-separated signal, and performs smoothing according to the smoothing parameters and the re-calculated mean envelope to generate a new smoothed mean envelope, and if the new smoothed mean envelope converges, then the processing unit determines the trend component or the non-trend component according to the smoothed mean envelope.

15. The signal processing apparatus according to claim 14, wherein the processing unit determines whether the standard deviation of the smoothed mean envelope is smaller than a default threshold, if the standard deviation of the smoothed mean envelope is smaller than the default threshold, then the processing unit determines that the mean envelope converges, and if the standard deviation of the smoothed mean envelope is not smaller than the default threshold, then the processing unit determines that the mean envelope does not converge.

16. The signal processing apparatus according to claim 14, wherein the processing unit determines whether the smoothed mean envelope converges according to Cauchy convergence test.

17. The signal processing apparatus according to claim 10, wherein the trend component accumulates smoothed mean envelopes.

18. The signal processing apparatus according to claim 10, wherein the trend component is obtained from a weight computation according to the difference between smoothed mean envelopes and the to-be-separated signal.

19. The signal processing apparatus according to claim 10, wherein the input interface and the processing unit are integrated as a functional chip.

20. The signal processing apparatus according to claim 19, further comprising a chip carrier used for carrying the functional chip.

21. The signal processing apparatus according to claim 20, wherein the chip carrier comprises:
    a signal sensing unit used for generating the to-be-separated signal according to a physiological signal; and an output interface used for outputting the to-be-separated signal to the input interface.

22. The signal processing apparatus according to claim 21, wherein the signal sensing unit comprises:
   a signal sensing element used for measuring the physiological signal;
   an analog front end (AFE) coupled to the signal sensing element for amplifying the physiological signal to generate an analog signal; and
   an analog-to-digital converter coupled with the output interface and used for converting the analog signal into the to-be-separated signal.

23. The signal processing apparatus according to claim 22, wherein the signal sensing element is a passive sensing element.

24. The signal processing apparatus according to claim 22, wherein the signal sensing element is an active sensing element.

25. The signal processing apparatus according to claim 22, wherein the chip carrier further comprises:
   a driving unit used for driving the signal sensing element; and
   a digital-to-analog converter used for controlling the driving unit.

26. The signal processing apparatus according to claim 22, wherein the chip carrier further comprises:
   a stretchable portion used for extending the signal sensing element.

27. The signal processing apparatus according to claim 22, wherein the chip carrier further comprises:
   an adhesive positioning portion set around the signal sensing element.

* * * * *